US008389793B2

(12) United States Patent
Cumming

(10) Patent No.: US 8,389,793 B2
(45) Date of Patent: Mar. 5, 2013

(54) METHODS FOR INCREASING THE DIVERSITY OF MONOCLONAL ANTIBODIES PRODUCED AGAINST AN ANTIGEN

(75) Inventor: Dale Anthony Cumming, Acton, MA (US)

(73) Assignee: Acton Biotech Consulting, Acton, MA (US)

( * ) Notice: Subject to any disclaimer, the term of this patent is extended or adjusted under 35 U.S.C. 154(b) by 294 days.

(21) Appl. No.: 12/640,771

(22) Filed: Dec. 17, 2009

(65) Prior Publication Data
US 2010/0162417 A1 Jun. 24, 2010

Related U.S. Application Data

(63) Continuation of application No. 11/248,315, filed on Oct. 12, 2005, now abandoned.

(60) Provisional application No. 60/617,859, filed on Oct. 12, 2004.

(51) Int. Cl.
C12P 21/08 (2006.01)

(52) U.S. Cl. .......................................... 800/4; 435/69.6

(58) Field of Classification Search ...... 800/4; 435/69.6
See application file for complete search history.

(56) References Cited

FOREIGN PATENT DOCUMENTS

| WO | WO 02/34041 | 5/2002 |
|---|---|---|
| WO | WO-2006/091515 A2 | 8/2006 |

OTHER PUBLICATIONS

Yin et al. (2002) "CTLA-4 Ig in combination with anti-CD40L prolongs xenograft survival and inhibits anti-Gal Ab production in GT-Ko mice," *American Journal of Transplantation*. 2: 41-47.
Asano, et al. "Growth Retardation and Early Death of β-1,4-galactosyltransferase Knockout Mice With Augmented Proliferation and Abnormal Differentiation of Epithelial Cells," *EMBO J.*, 16: 1850-1857, 1997.
Borrebaeck and Olin, "Antibody Evolution Beyond Nature," *Nature Biotechnology*, 20: 1189-1190, 2002.
Bowes, et al., "Tolerance to Self Gangliosides Is the Major Factor Restricting the Antibody Response to Lipopolysaccharide Core Oligosaccharides in *Campylobacter jejuni* Strains Associated With Guillain-Barre Syndrome," *Infect. Immun.*, 70: 5008-5018, 2002.
Declerck, et al., "Generation of Monoclonal Antobodies Against Autologous Proteins in Gene-inactivated Mice," *J. Bio. Chem.*, 270: 8397-8400, 1995.
Ellies, et al., "Core 2 Oligosaccharides Biosynthesis Distinguishes Between Selectin Ligands Essential for Leukocyte Homing and Inflammation," *Immunity*, 9: 881-890, 1998.
Granovsky, et al., "Suppression of Tumor Growth and Metastasis in Mgat5-deficient Mice," *Nature Medicine*, 6: 306-312, 2000.
Kido, et al., "Presence of Polysialic Acid and HNK-1 Carbohydrate on Brain Glycoproteins From β-1,4-Galactosyltransferase- Knockout Mice," *Biochem. Biophys. Res. Commun.*, 245: 860-864, 1998.
Kotani, et al., "Impaired Galactosylation of Core 2 O-Glycans in Erythrocytes of β1, 4-Galactosyltransferase Knockout Mice," *Biochem. Biophys. Res. Commun.*, 260: 94-98, 1999.
Kotani, et al,, "Knockout of Mouse β1, 4-Galactosyltransferase-1 Gene Results in a Dramatic Shift of Outer Chain Moieties of N-glycans From Type 2 to Type 1 Chains in Hepatic Membrane and Plasma Glycoproteins," *Biochem J.*, 357: 827-834, 2001.
Lunn, et al., "High-Affinity Anti-Ganglioside IgG Antibodies Raised in Complex Ganglioside Knockout Mice: Reexamination of GD1a Immunolocalization," *J. Neurochem.*, 75: 404-412, 2000.
Lu, et al., "Targeted Mutation in β1, 4-Galactosyltransferase Leads to Pituitary Insufficiency and Neonatal Lethality," *Dev. Biol.* 181: 257-267, 1997.
Schnaar, et al., "Immunoglobulin G-Class Mouse Monoclonal Antibodies to Major Brain Gangliosides," *Anal Biochem.*, 302: 276-284, 2002.
Sperandio, et al., "Severe Impairment of Leukocyte Rolling in Venules of Core 2 Glucosaminyltransferase-Deficient Mice," *Blood*, 97: 3812-3819, 2001.
International Search Report for PCT/US2005/036450.
Cumming, Glycobiology 1:115-130 (1991).
Radcliffe et al., J. Biol. Chem. 282:7405-7415 (2007).
Leung et al., Int. J. Cancer 60:534-538 (1995).
Sato et al., Hum. Antibodies Hybridomas 7:175-183 (1996).
Wright et al. EMBO J. 10:2717-2723 (1991).
Leibiger et al., Biochem. J. 338:529-538 (1999).
Glycoconj. J. 2002, 19(3):211-219.
Werner et al. Acta Paediatr. Suppl. 96(455):17-22 (2007)).
Coloma et al. (Molec. Immunol. 37:1081-1090 (2000)).
Wright et al (Springer Semin Immunopathology ,15 :259-273 (1993)).
Detente (Trends in Biotechnology 3, letters to editor, No. 9, (1985)).
Olden et al (Biochem et Biophys Acta 650:209-232 (1982)).
Chen et al. (Molec. Immunol. 37:455-466 (2000).
Calarese et al. (Science 300:2065-2071 (2003).

*Primary Examiner* — Lynn Bristol
(74) *Attorney, Agent, or Firm* — Charles E. Lyon; Robert N. Sahr; Choate, Hall & Stewart LLP

(57) ABSTRACT

The present invention relates to methods for increasing the diversity of monoclonal antibodies produced against an antigen. The methods of the invention utilize immunization of a murine host defective in one or more enzymes involved in a post-translational modification of a polypeptide or a modification of a lipid, wherein said modification is exposed on a cell surface. The invention also relates to monoclonal antibodies produced by these methods and which are not produced when a normal mouse is immunized with the same antigen. The invention further relates to compositions comprising these monoclonal antibodies, as well as to such monoclonal antibodies bound or conjugated to a toxin, a detectable marker or to a solid support.

7 Claims, 2 Drawing Sheets

METHODS FOR INCREASING THE DIVERSITY OF MONOCLONAL ANTIBODIES PRODUCED AGAINST AN ANTIGEN

PRIORITY INFORMATION

The present application is a continuation application of non-provisional application U.S. Ser. No. 11/248,315, filed on Oct. 12, 2005, which claims priority to provisional application U.S. Ser. No. 60/617,859 filed Oct. 12, 2004. The entire contents of each of these priority applications is hereby incorporated by reference.

TECHNICAL FIELD OF THE INVENTION

The present invention relates to methods for increasing the diversity of monoclonal antibodies produced against an antigen. The methods of the invention utilize immunization of a murine host defective in one or more enzymes involved in a post-translational modification of a polypeptide or a modification of a lipid, wherein said modification is exposed on a cell surface. The invention also relates to monoclonal antibodies produced by these methods and which are not produced when a normal mouse is immunized with the same antigen. The invention further relates to compositions comprising these monoclonal antibodies, as well as to such monoclonal antibodies bound or conjugated to a toxin, a detectable marker or to a solid support.

BACKGROUND OF THE INVENTION

The use of monoclonal antibodies ("mAbs") as therapeutic treatment for a variety of diseases and disorders is rapidly increasing because they have been shown to be safe and efficacious therapeutic agents. Approved therapeutic monoclonal antibodies in the United States include ReoPro® (for patients undergoing high-risk coronary angioplasty to prevent recurrent coronary obstruction), Herceptin (for treatment of metastatic breast cancer), Zenapax (for prevention of acute kidney transplant rejection), Synagis (for the treatment of RSV-induced lower respiratory tract disease), Rituxan (for treatment of B cell non-Hodgkin's lymphoma), Campath (for treatment of B cell chronic lymphocytic leukemia), Humira (for the treatment of rheumatoid arthritis) and Remicade (for the treatment of Crohn's Disease). Many more monoclonal antibodies are in various phases of clinical development for a variety of diseases. Perhaps the most prevalent of these potential therapeutics are monoclonal antibodies that target various forms of cancer.

Monoclonal antibodies are typically generated in non-human mammals, most frequently the mouse, by administration of an "immunogen" (a substance or mixture of substances that elicit an antibody response) and subsequent isolation of B-cells that make antibodies. The B-cells are then immortalized by fusion to another, stable cell type to create a "hybridoma". A central tenet of modern immunology is that an individual B-cell makes one specific antibody that is defined by its primary amino acid sequence and its underlying gene sequence. In other words, each B-cell is clonal and therefore each immortalized hybridoma will make only one specific antibody. Moreover, the ability of a given antibody to bind to an antigen (a foreign entity to the body) is mediated largely by six peptide loops carried on the two prototypical chains that make up an antibody (termed the "heavy" and light" chains). These peptide loops cause the antibody to bind to specific portions (epitopes) of an antigen. Because the binding of antibodies to their epitopes is that of two complementary surfaces interacting, these six peptide loops are termed complementary determining regions, or CDRs.

The therapeutic utility of murine mAbs has been found to be limited, principally due to the fact that human patients mount their own antibody response to murine proteins, including murine mAbs. This so-called HAMA (human anti-mouse antibody) response results in the eventual neutralization and elimination of murine mAbs, rendering these mAbs therapeutically ineffective after only a few administrations. One solution to this problem involves a process termed "humanization" where, in its simplest terms, the murine CDRs of an antibody are "grafted" onto the framework of a human antibody. Advances in the ability to "humanize" monoclonal antibodies have greatly contributed to the efficacy of these molecules as therapeutics. Humanization prevents or greatly delays the patient developing an immune response against the administered therapeutic monoclonal antibody and extends the half-life of that antibody in circulation.

With this solution, one of the major remaining limitations to deriving therapeutic antibodies to a particular antigen is the ability to obtain a mAb that recognizes a desired epitope. Many therapeutic target antigens are poorly immunogenic. They are incapable of stimulating target-specific monoclonal antibody production. The ability of a mouse or a human to recognize an antigen and mount an antibody response is determined in part by its antibody diversity.

The intrinsic antibody diversity in mice and humans is large, but not infinite. Overall, antibody diversity is defined by five steps.

Step 1—Rearrangement of an inherited set of gene segments (termed V, D, or J gene segments) that make up the variable region of immunoglobulin heavy or light chains. Each individual inherits multiple copies of the V, D, and J gene segments and different combinations of these give rise to different heavy or light chains. This process is known as somatic recombination and is tightly regulated as the B cell develops from a hematopoietic stem cell to a pro-B cell, then a pre-B cell and finally to an "immature" B-cell that expresses a specific IgM molecule on its surface.

Step 2—Different combinations of heavy and light chains give rise to different antigen-binding sites (one prototypical immunoglobulin). In theory, these first two processes could give rise to about 3.5 million different antibody specificities in humans (in "Immunobiology: The Immune System in Health and Disease," $4^{th}$ Edition, C. A Janeway, P. Travers, and M. Walport [eds.] Garland Publishing, New York, 1999).

Step 3—Additional diversity is then generated by a process that randomly inserts or deletes nucleotides in the third CDR region where different constituent gene segments join. The result of this "functional diversity" is often (roughly 2 out of 3 times) a disruption of the reading frame and the production of a non-functional protein. All mechanisms for generating diversity described so far occur during the development of B cells in the bone marrow. At this point, the maturation of the B cell has progressed from a stem cell to an "immature" B cell.

Step 4—The antibody repertoire is then edited (reduced) by elimination of immature B cells attempting to produce unstable antibodies or the removal of immature B cells that recognize "self". The latter point is crucial in order to avoid the immune system attacking the organism's own body. This editing of the repertoire occurs for the immature B cell both in the bone marrow and as the B cells first migrate to secondary lymphoid tissue. After further development to full maturation, a population of naïve B cells exists in the periphery that can engage antigens with low affinity. The repertoire of antigen binding sites represented by this population can be thought of as "shape templates" seeking an initial match against foreign antigens. Any naïve B cell that successfully matches an epitope on an antigen is selectively stimulated to proliferate—a process known as positive selection.

Step 5—A final source of immunoglobulin diversity derives from a process known as somatic hypermutation. This process introduces point mutations into the V regions of immunoglobulin genes upon encounter of a mature B cell with an antigen. This mutation of the immunoglobulin gene occurs at a very high rate and results in expression of altered immunoglobulin molecules on the surface of the B cell. Some of these altered immunoglobulins will bind antigen even better than the original and are preferentially selected to mature into antibody-secreting cells. This latter process is known as affinity maturation.

One of the potential reasons that a foreign antigen is poorly immunogenic is that the immune system of a mouse will not produce antibodies against a self-antigen (an antigen that is normally produced by that mouse). If the antigen representing a desired therapeutic target (e.g. a viral or bacterial protein or fragment thereof or a human or other mammalian protein) shares one or more epitopes with a self-antigen, no monoclonal antibodies will be generated against those epitopes. Many pathogens seek to avoid destruction by the host immune system by "masking" their surfaces with host self-antigens.

Returning to Step 4, above, when an immature B cell encounters a self-antigen, it has four possible fates—each of which insure that it will not mature and enter into the animal's circulation. One fate is cell death by apoptosis. This is also known as clonal deletion and is typical for B cells that interact with multivalent self-antigens, such as multiple copies of an MHC molecule on a cell surface. A second potential fate is called receptor editing. In this scenario, the self-reactive B cell can be rescued by further gene rearrangements in immunoglobulin light chains such that the cell no longer produces an antibody against self-antigens.

Self-reactive B cells that recognize smaller antigens respond differently. These cells tend to be inactivated and enter a state of anergy, or permanent unresponsiveness. Such cells do ultimately end up in circulation, but are short-lived and incapable of producing antibodies against self-antigens. The fourth potential fate is that the B cell remains in a state of immunological "ignorance" of the self-antigen. These cells, which may actually be very weakly reactive with self-antigens, enter the circulation and have been speculated to be the source of autoimmune disease.

Thus, the naïve B-cells entering circulation represent one level of antibody diversity, a level of diversity reduced relative to that specified at the genomic level. The cell surface IgM's clonally expressed on each B-cell have a defined three dimensional shape in their antigen binding site (a shape template) that can potentially interact with a complementary shape on a foreign antigen. The ensemble of all B-cells that have exited the bone marrow thus define a repertoire of "shape templates" that make the initial encounter with foreign antigens.

When a foreign antigen is encountered, those naïve B-cells whose surface IgM is complementary with some part of the antigen surface (an epitope) receive intracellular signals to proliferate. This positive selection of a limited subset of circulating B-cells insures adequate numbers of reactive B-cells are produced to overwhelm the foreign agent. Further antibody diversity then ensues (in tandem with selective proliferation) through a process known as somatic hypermutation. In this process, random nucleic acid substitutions are made in the region coding for the antigen-binding site and further positive selection is made for those new antibodies that bind with higher affinity to the antigen (better and/or more extensive shape complementation between the B-cell's surface immunoglobulin and the antigen). Somatic hypermutation has been estimated to expand the ultimate scope of antibody diversity 10 to 100-fold or more. Thus, any process that can expand the repertoire of "shape templates" will result in a disproportionate expansion (through somatic hypermutation) in the ultimate scope of antibody diversity in a mouse or human that can respond to a foreign antigen.

Post-translational modification of proteins, such as glycosylation, sulfation, acetylation and proteolytic processing, and modification of lipids, such as glycosylation, result in antigenic epitopes that can be recognized by monoclonal antibodies. Because many of these same modifications are present on self-antigens, such epitopes do not typically stimulate antibody production in a normal, wild-type mouse. However, mice that are defective in one or more enzymes involved in such modifications (knockout mice) will produce native proteins and lipids with altered modifications (truncated, altered or complete lack of the modification). These knockout mice are capable of generating an antibody response to corresponding wild-type modified proteins and lipids because their immune system does not see such molecules as self-antigens. Such antibodies may be generated by the wild-type protein or lipid or, in some cases, by foreign antigens that share epitopes with the wild-type protein or lipid.

Recent experiments have confirmed this in an experiment designed to generate antibodies to naturally occurring murine brain gangliosides (glycolipids) in order to study the expression and function of these molecules, as well as ganglioside-related pathologies (R. L. Schnaar et al., *Anal Biochem.,* 302, pp. 276-284 (2002)). This group demonstrated that immunization of mice defective in a key enzyme in major brain ganglioside biosynthesis (UDP-GalNAc:GM3/GD3 N-acetylgalactosaminyltransferase) with wild-type gangliosides resulted in the production monoclonal antibodies that recognized those wild-type gangliosides. Similar immunization of wild-type mice did not result in the production of any monoclonal antibodies that recognized the wild-type gangliosides. Similar results were also obtained by another group using mice knocked out for the same gene (M. P. T. Lunn et al., *J. Neurochem.,* 75, pp. 404-12 (2000).

Another group used lipopolysaccharides from the bacteria *C. jejuni* were used as an antigen to raise antibodies in the same knockout mouse. Those mice produced antibodies that cross-reacted with those wild-type mouse gangliosides which were lacking in the knockout mouse (T. Bowes et al., *Infect. Immun.,* 70, pp. 5008-18 (2002). The same antigens in wild-type mice did not produce a significant antibody response against either the antigen itself or any mouse gangliosides.

In addition, knockout mice with targeted inactivation of post-translational modifications will possess naïve B cells with an increased repertoire of "shape templates" that initially engage antigens. If these additional "shape templates" interact with foreign antigens, whatever the composition of the epitope, the process of somatic hypermutation will greatly amplify the diversity of antibodies made in response to that antigen as compared to the wild type mouse and these additional antibodies will be unique to the knockout mouse.

Despite the advances that have been made in generating therapeutically effective monoclonal antibodies, there still exists a need for generating a greater diversity of monoclonal antibodies against therapeutically important targets (C. A. K. Borrebaeck and M. Olin (2002) *Nature Biotechnology* 20:1189-1190). Because human disease is often marked by the utilization of some aspect of "self" to avoid host immune surveillance or as a consequence of the pathological process, there is a need for methods of generating monoclonal antibodies against targets that share epitopes with self antigens and which cannot be produced using wild-type mice.

SUMMARY OF THE INVENTION

The present invention solves the problem set forth above by providing methods for obtaining monoclonal antibodies to antigens that could not be obtained using known monoclonal antibody production techniques. The invention is based upon the fact that mice defective in one or more enzymes responsible for post-translational modifications of proteins and modification of lipids ("knockout mice" or "KO mice") have circulating B cells that recognize and produce antibodies to properly modified murine proteins and lipids. Mice that do not contain such defects in their protein and lipid modification machinery (hereinafter "wild-type mice") will not produce antibodies against properly modified murine proteins and lipids. This is because the immune system of wild-type mice recognizes all properly modified molecules as "self" and therefore will not make antibodies to such molecules.

The inability of wild-type mice to make antibodies directed to "self" molecules also renders those animal incapable of generating antibodies to any epitope on a foreign antigen that shares the same structure as "self" molecules. Knockout mice generate a different set of "self" molecules due to their enzymatic defect. Accordingly, such KO mice have the capability of generating antibodies to epitopes that have the same structure as present in wild-type "self" molecules if those molecules are altered in the KO mice because of the enzymatic deficiency.

Moreover, the conformation of the defective modified molecules produced by KO mice could be different from that of the corresponding, properly modified molecules. Such a conformational change is expected to result in the differential accessibility to the immune system of certain epitopes on that modified molecule, as compared to properly modified molecules. Thus, the KO mouse immune system does not see these now "hidden" epitopes as "self" and antibodies to such normally exposed epitopes can be generated. As above, if a foreign antigen contains such an epitope, antibodies to that epitope cannot be produced in wild-type mice. Moreover, if the altered conformation of a molecule is pervasive in the KO mouse (no wild type conformers present), then the wild type conformation itself may be antigenic in the KO mouse.

Finally, such KO mice will possess an increased repertoire of "shape templates" (in the form of naïve circulating B cells) that can respond to foreign antigens when such antigens possess an epitope whose three dimensional shape is sufficiently complementary to the novel templates, regardless of whether said antigen actually contains the deficient elements of self. For example, an infecting virus may contain protein epitopes that mimic the three-dimensional shape of carbohydrate self-antigens present in wild type mice but absent in a KO mouse. As above, antibodies to such epitopes are not typically produced in wild type mice.

Based upon the above, the invention provides a method of increasing the diversity of monoclonal antibodies that bind to a molecule of interest comprising the steps of: a) immunizing a murine host with an antigen that comprises an epitope present on said molecule in a manner sufficient for said host to develop antibodies against said antigen, wherein said host comprises a knockout mutation in an enzyme involved in a post-translational modification of a polypeptide or a modification of a lipid, said modification being exposed on a cell surface; and wherein said molecule of interest is not present in a murine host; b) isolating the splenocytes from said immunized host and fusing said splenocytes with immortalized cells to form a hybridoma; and c) assaying individual hybridoma cells to determine if said cell produces a monoclonal antibody that bind to said molecule.

The invention also provides an improvement in a method of producing monoclonal antibodies that bind to a molecule of interest comprising the steps of immunizing a murine host with an antigen that comprises an epitope present on said molecule; allowing the host to develop antibodies to said antigen; isolating the splenocytes of said host; fusing said splenocytes with immortalized cells to form a hybridoma; and assaying individual hybridoma cells to determine if said hybridoma cell produces a monoclonal antibody that binds to said molecule, wherein the improvement comprises utilizing a murine host comprising a knockout mutation in an enzyme involved in a post-translational modification of a polypeptide or a modification of a lipid, said modification being exposed on a cell surface.

The invention also provides a hybridoma comprising a B cell from a murine host that has been immunized with an antigen that comprises an epitope present on a molecule of interest, wherein said host comprises a knockout mutation in an enzyme involved in a post-translational modification of a polypeptide or a modification of a lipid, said modification being exposed on a cell surface fused to an immortalized cell, wherein said hybridoma produces a monoclonal antibody characterized in that it: a) binds to said molecule of interest; and b) is not produced by a hybridoma comprising a B cell from a murine host normal in said enzyme that is immunized with said antigen fused to an immortalized cell. The above hybridoma may be used in a method to produce monoclonal antibodies by standard techniques.

The invention also provides a monoclonal antibody produced by the above hybridoma, as well as derivatives thereof. The monoclonal antibody and its derivatives may be used in diagnostic and therapeutic applications.

DETAILED DESCRIPTION OF CERTAIN EMBODIMENTS OF THE INVENTION

Figure 1:
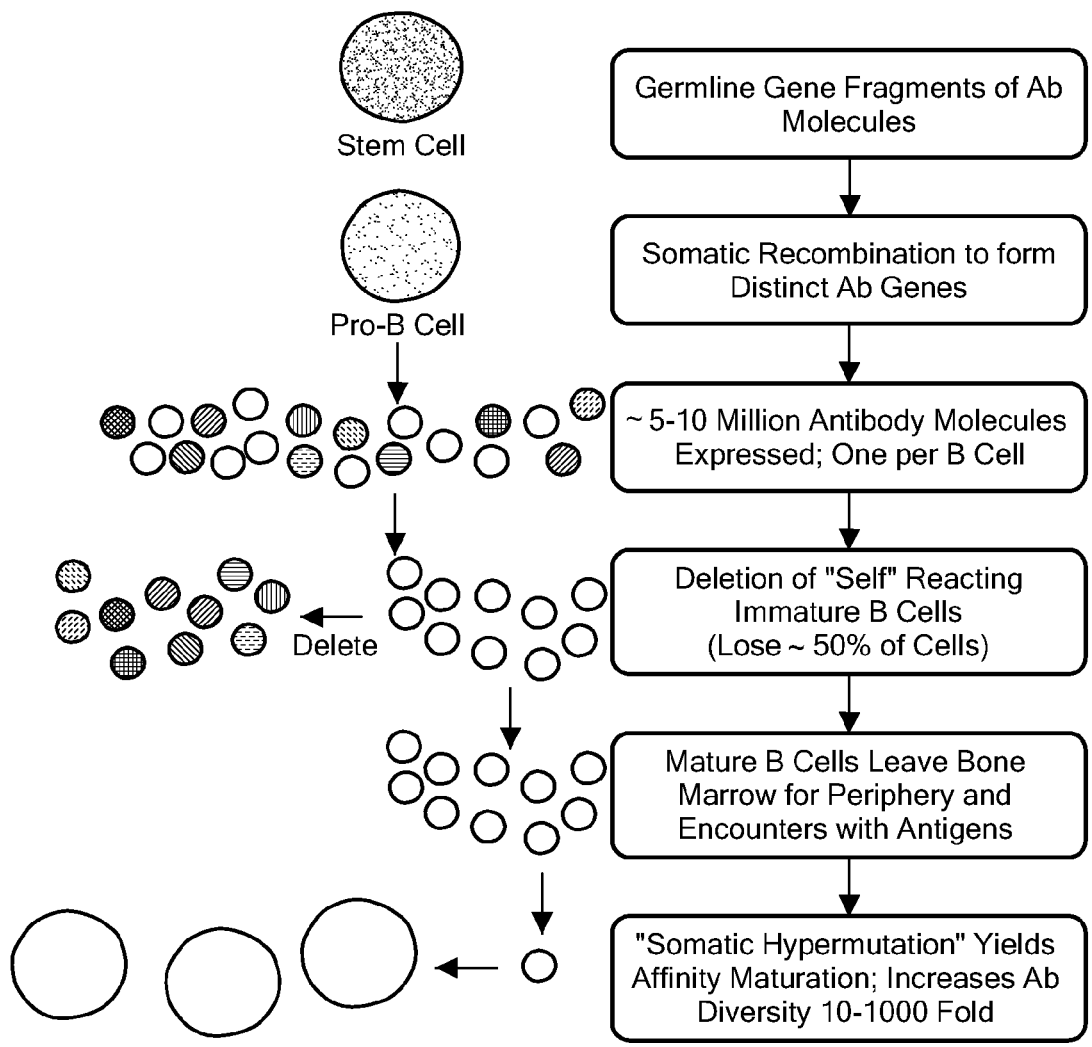
FIG. 1 depicts the multi-step process that defines the antibody repertoire in wild type mice. Generation of antibody diversity occurs through 5 Major Steps: Step 1—Somatic Recombination. Ig gene fragments assembled. Step 2—Pairing of heavy and light chains give rise to different antigen binding sites (one prototypical immunoglobulin). In theory, these first two processes could give rise to about 3.5 million different antibody specificities in humans. Step 3—Additional diversity is then generated by a process which randomly inserts or deletes nucleotides in the third CDR region where different constituent gene segments join. Step 4—Elimination of immature B cells attempting to produce unstable antibodies and the removal of immature B cells that recognize "self". Step 5—Somatic Hypermutation; In the presence of antigen "class switching" occurs as well.
Figure 2:
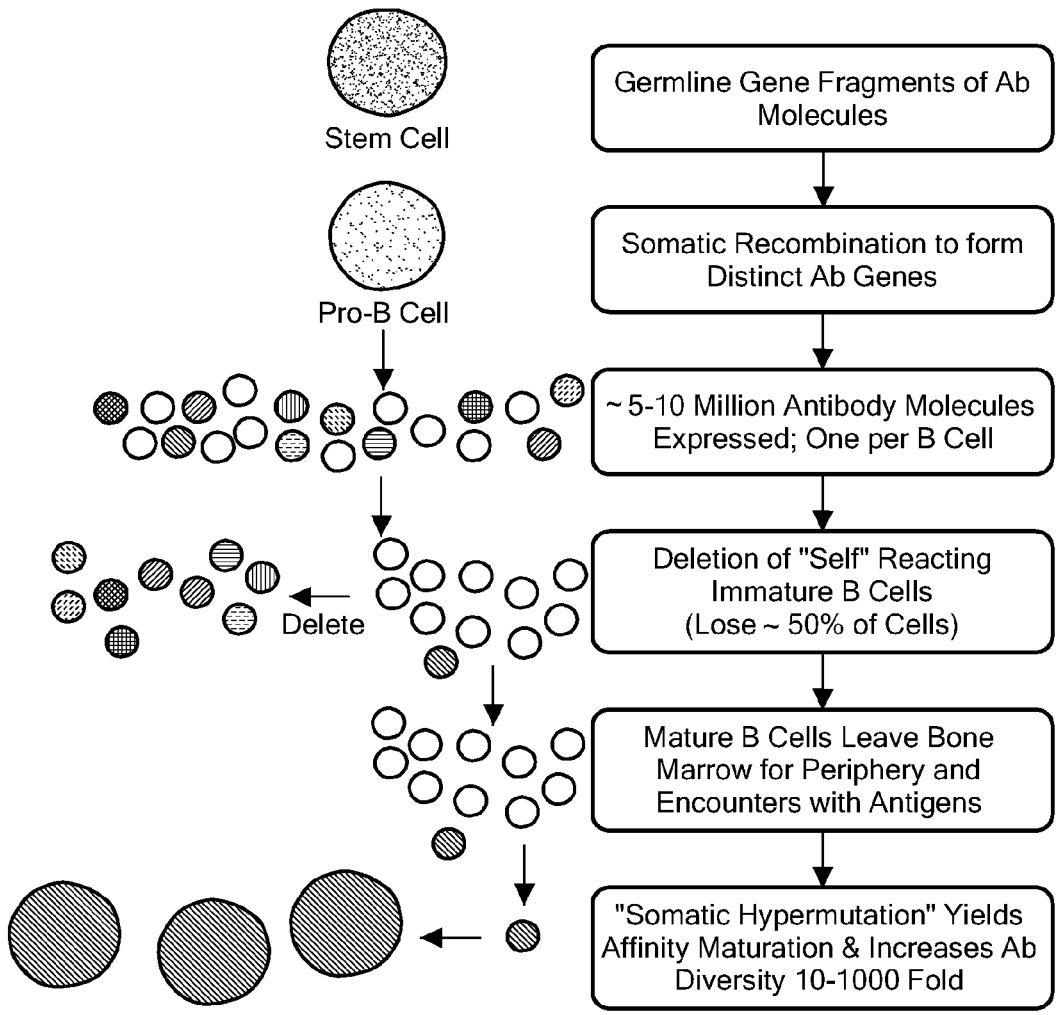
FIG. 2 depicts multi-step process that defines the altered antibody repertoire in KO mice. Glycosylation and other post-translational modifications are well known determinants of "self". Thus, targeted deletion of enzymes involved in post-translational modifications will alter (slightly) that mouse strain's sense of self as compared to wild-type mouse. This results in an enhancement of the naïve B cell repertoire that is magnified further by somatic hypermutation upon contact with antigen. Novel, unique and potent antibodies result.

According to one embodiment, the invention provides a method of increasing the diversity of monoclonal antibodies that bind to a molecule of interest comprising the steps of: a) immunizing a murine host with an antigen that comprises an epitope present on said molecule in a manner sufficient for said host to develop antibodies against said antigen, wherein said host comprises a knockout mutation in an enzyme involved in a post-translational modification of a polypeptide or a modification of a lipid, said modification being exposed on a cell surface; and wherein said molecule of interest is not naturally present in a murine host; b) isolating the splenocytes from said immunized host and fusing said splenocytes with immortalized cells to form a hybridoma; and c) assaying individual hybridoma cells to determine if said cell produces a monoclonal antibody that bind to said molecule.

In a preferred embodiment, the knockout mutation is in an enzyme selected from a glycosyltransferase, a sulfotransferase, a protease involved in proteolytic processing, or an acetyltransferase. More preferably, the mutation is in a glycosyltransferase. Even more preferably, the mutation is in mannosyl($\alpha$-1,6-)-glycoprotein $\beta$-1,6-N-acetyl-glucosaminyltransferase V (MGAT5; GNT-V), core 2 $\beta$1-6N-acetylglucosaminyltransferase (C2 GlcNAcT) or $\beta$(1,4)-galactosyltransferase I ($\beta$4GalT-I).

Glycosyltransferases that may be knocked out in a murine host according to this invention include, but are not limited to core 2 $\beta$1,6-N-acetylglucosaminyl transferase, mannosyl($\alpha$-1,6-)-glycoprotein $\beta$-1,6-N-acetylglucosaminyltransferase V, N-acetylglucosaminyltransferase III, N-acetylgalactosaminyltransferases I-IX, fucosyltransferases III-VII, galactosyltransferase I, and the ganglioside specific UDPGalNAc:GM3/GD3 N-acetylgalactosaminyltransferase.

Sulfotransferases that may be knocked out in a murine host according to this invention include, but are not limited to the GalNAc/GlcNAc-6-O-sulfotransferase [GST] family (e.g. GST-1, 2, & -3; J. R. Grunwell et al., (2002) *Biochemistry* 41:15590-600; J. K. Lee et al., (2003) *Glycobiology* 13:245-54; J. R. Grunwell and C. R. Bertozzi (2002) *Biochemistry* 2002 41:13117-26), the heparan sulfate-2-O-sulfotransferase (C. L. Merry and V. A. Wilson (2002) *Biochim Biophys Acta.* 1573:319-27), members of the family of N-acetylglucosamine N-deacetylase/N-sulfotransferases [NDST] (K. Grobe et al., (2002) *Biochim Biophys Acta.* 1573:209-15), and galactosylceramide sulphotransferase (M. Eckhardt et al., (2002) *Biochem J.* 368(Pt 1):317-24).

Proteases involved in proteolytic processing that may be knocked out in a murine host according to this invention include, but are not limited to, the mammalian subtilisin-like proprotein convertases (e.g. furin, PC1, PC2, PC4, PACE4, PC5 (and its isoform PC5B), and PC7, as well as the convertase SKI-1 (G. Siegfried et. al., (2003) *J. Clin. Invest.* 111: 1723-1732), the ADAM (a disintegrin and metalloproteinase) family of enzymes that includes TACE [Tumor necrosis factor-alpha converting enzyme; ADAM17] (K. Endres et al., (2003) *Eur J Biochem.* 270:2386-93), as well as the ADAMTS family of proteases (B. L. Tang and W. Hong (1999) FEBS Lett. 445:223-5).

Acetyltransferases that may be knocked out in a murine host according to this invention include, but are not limited to the 7-0 or 9-O-acetyltransferases that modify sialic acid (W. X. Shi et al., (1998) *Glycobiology* 8:199-205; H. Satake et al., (2003) *J. Biol. Chem.* 278:7942-8.)

Mice containing knockouts in any of the above enzymes may be created using methods well known in the art. The general technique involves identifying and isolating DNA encoding the gene to be knocked out. That DNA is then modified so that it no longer encodes a functional enzyme. Such modification includes deletion of segments of the DNA, insertion of non-coding DNA into the coding portion of the DNA and substitution of portions of the DNA with non-coding or nonsense DNA. The modified gene is then placed in an appropriate vector and used to transfect mouse embryonic stem ("ES") cells in culture. Some of the transfected cells exchange the defective DNA for the normal gene through homologous recombination. Such cells are typically selected for through a marker gene present in the vector that also gets incorporated into the mouse ES genome through the homologous recombination event.

ES cells containing the "knocked out" gene are expanded in culture and then microinjected into a mouse embryo that is subsequently implanted into a female mouse. Thus, the embryo represents a chimera of normal ES cells and knocked out ES cells. The offspring from these chimeric embryos are crossbred and offspring from those cross-breedings are also crossbred to ultimately obtain mice that are homozygous for the desired knockout.

Knockout mice may also be commercially obtained either from existing populations or created de novo and tailored to knockout a desired gene. Such strains and services are available from many companies, such as Lexicon, Deltagen, Cell and Molecular Technologies, and Taconic Labs.

Knockout mice may also be created using small interfering RNAs (siRNAs) to produce "knock down" mice. Methods to generate such "knock down" mice are well known in the literature and such mice are reported to recapitulate the phenotype of null mice produced by traditional "knockout" technology (T. Kunath et al., (2003) *Nature Biotechnol.* 21: 559-561; H. Hasuwa et al., (2002) *FEBS Lett.* 532:227-230; M. A Carmell et al., (2003) *Nat. Struct. Biol.* 10:91-92; D. A. Rubinson, et al. (2003) *Nat. Genet.* 33:401-406; G. Tiscornia et al., (2003) *Proc. Natl. Acad. Sci. USA* 100:1844-1848.)

The requirement that the knockout be in an enzyme involved in a post-translational modification of a polypeptide or a modification of a lipid, said modification being exposed on a cell surface or secreted extracellularly is due to the fact that the process by which the host distinguishes between "self" and foreign molecules is based upon what can bind to the IgM molecules present on the surface of immature B-cells, i.e. molecules exposed on other cell membranes or present in the extracellular milieu. Accordingly, knockout mice which do not manifest their defective modifications on the cell surface or on secreted molecules will have the same set of "self" epitopes as a wild-type mouse and thus will not produce a different set of antibodies from a wild-type mouse.

Once the knockout mouse has been provided, it can be immunized with an antigen that comprises an epitope present on a molecule of interest. A "molecule of interest" according to the present invention is any molecule that is not found naturally in an uninfected murine host. The term includes proteins, glycoproteins, lipoproteins, lipids, glycolipids and even nucleic acid molecules. It further includes compounds found in other mammals, and molecules found in pathogens, such as viruses, bacteria and fungi. The molecule of interest can be free, part of a mixture, present on the surface of a cell, or contained within a tissue sample. Preferably, a molecule of interest is one that is believed to play a role in mammalian disease or disorder, most preferably a human disease or disorder.

The term "not found naturally in a murine host" means that the molecule of interest is not encoded by a naturally occurring murine gene or expressed in a wild-type or knockout mouse.

The choice of antigen with which to immunize the KO mouse can be made from the entire intact molecule of interest or any fragment thereof sufficiently large to be antigenic. It also includes any of the foregoing complexed with another agent designed to increase antigenicity. Such antigenicity enhancers include, but are not limited to, KLH, ovalbumin, albumin, and polyacrylamide. Alternatively the choice of antigen can be made from molecules that are related to or mimic epitopes on the molecule of interest.

In a preferred embodiment, the antigen is selected from a preparation containing the molecule of interest or fragments thereof (such as a cell membrane preparation, a viral envelope preparation, a bacterial cell wall preparation, or a nucleic acid extract from a cell, bacteria or virus), the isolated molecule of interest itself, or an isolated fragment of the molecule of interest (such as a peptide fragment, a portion of the carbohydrate moiety on a molecule of interest that is a glycoprotein or glycolipids, or an oligonucleotide or polynucleotide protein of a nucleic acid molecule of interest). Even more preferred is when the antigen is selected from a leukocyte cell surface antigen, a viral envelope antigen, or a cancer cell membrane antigen. Most preferred is when the antigen is selected from isolated P-selectin glycoprotein ligand-1 (PSGL-1), a membrane preparation from a human breast cancer tumor or isolated HIV viral envelope gp120.

The step of immunizing the KO mouse with an antigen may be carried out in any manner well known in the art for stimulating the production of antibodies in a mouse (see, for example, E. Harlow and D. Lane, *Antibodies: A Laboratory Manual*, Cold Spring Harbor Laboratory Press, Cold Spring Harbor, N.Y. (1988)). This includes suspending or dissolving the antigen in a buffer, optionally with an adjuvant, such as complete Freund's adjuvant. The amount of antigen, types of buffers and amounts of adjuvant are well known to those of skill in the art and are not limiting in any way on the present invention. These parameters may be different for different antigens, but are easily elucidated.

Similarly, the location and frequency of immunization sufficient to stimulate the production of antibodies is also well known in the art. In a typical immunization protocol, mice are injected intraperitoneally with antigen on day 1 and again about a week later. This is followed by booster injections of the antigen around day 14. The booster injections typically lack any additional adjuvant, are performed intravenously and may be repeated for several consecutive days. This protocol results in the production of antigen-specific antibody-producing B cells after about 16 days. Other protocols may also be utilized as long as they result in the production of B cells expressing an antibody directed to the antigen used in immunization.

In an alternate embodiment, lymphocytes from the unimmunized KO mouse are isolated, grown in vitro, and then exposed to the antigen in cell culture. The lymphocytes are then harvested and the fusion step described below in carried out. The next step in this method is the isolation of splenocytes from the immunized mouse and the subsequent fusion of those splenocytes with an immortalized cell in order to form an antibody-producing hybridoma. The isolation of splenocytes from a mouse is well-known in the art and typically involves removing the spleen from an anesthetized mouse, cutting it into small pieces and squeezing the splenocytes from the splenic capsule and through a nylon mesh of a cell strainer into an appropriate buffer so as to produce a single cell suspension. The cells are washed, centrifuged and resuspended in a buffer that lyases any red blood cells. The solution is again centrifuged and remaining lymphocytes in the pellet are finally resuspended in fresh buffer.

Once isolated and present in single cell suspension, the lymphocytes are fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors available from the Salk Institute Cell Distribution Center, San Diego, Calif. U.S.A., and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

The hybridomas are typically grown on a feeder layer of macrophages. The macrophages are preferably from littermates of the mice used to isolate splenocytes and are typically primed with incomplete Freund's adjuvant or the like several days before plating the hybridomas. Fusion methods are described in (Goding, "Monoclonal Antibodies: Principles and Practice," pp. 59-103 (Academic Press, 1986)), the disclosure of which is herein incorporated by reference.

The cells are allowed to grow in the selection media for sufficient time for colony formation and antibody production. This is usually between 7 and 14 days. The hybridoma colonies are then assayed for the production of antibodies specific for the molecule of interest. The assay is typically a colorimetric ELISA-type assay, although any assay may be employed that can be adapted to the wells that the hybridomas are grown in. Other assays include immunoprecipitation and radioimmunoassay. The wells positive for the desired antibody production are examined to determine is one or more distinct colonies are present. If more than one colony is present, the cells may be re-cloned and grown to ensure that only a single cell has given rise to the colony producing the desired antibody. Positive wells with a single apparent colony are typically recloned and re-assayed to insure only one monoclonal antibody is being detected and produced.

In a preferred embodiment, the murine host has a knockout mutation in an enzyme selected from a glycosyltransferase, a sulfotransferase, a protease involved in proteolytic processing, or an acetyltransferase. Even more preferred is a murine host having a knockout mutation in Golgi β1,6N-acetylglucosaminyltransferase V (MGAT5) and a mouse having a knockout mutation in core 2 β1-6N-acetylglucosaminyltransferase (C2 GlcNAcT). These two enzymes are glycosyltransferases. Knockout mice carrying these mutations are known in the art. The C2 GlcNacT knockout is described in L. G. Ellies et al., *Immunity*, 9, pp. 881-90 (1998), which is herein incorporated by reference. The MGAT5 knockout mouse is described in M. Granovsky et al., *Nature Medicine*, 6, pp. 306-12 (2000), which is herein incorporated by reference.

The method set forth above is similar to standard methods of making monoclonal antibodies known in the art, with the improvement being the use of the specific knockout mice set forth above. The improvement results in a subset of monoclonal antibodies that cannot be produced in wild-type mice due to the elimination of certain self-antigen recognizing B cells.

According to another embodiment, the invention provides a hybridoma comprising a B cell from a murine host that has been immunized with an antigen that comprises an epitope present on a molecule of interest, wherein said host comprises a knockout mutation in an enzyme involved in a post-translational modification of a polypeptide or a modification of a lipid, said modification being exposed on a cell surface fused to an immortalized cell, wherein said hybridoma produces a monoclonal antibody characterized in that it: a) binds to said molecule of interest; and b) is not produced by a hybridoma comprising a B cell from a murine host normal in said enzyme that has been immunized with said antigen, fused to an immortalized cell. Such monoclonal antibodies are hereinafter referred to as "KO unique Mabs."

The hybridoma according to this invention is created as described above by the fusion of splenocytes from the immunized mouse with an immortal cell line. Hybridomas produced by this fusion are screened for the presence of an antibody that recognizes the molecule of interest as previously set forth. In order to determine if the antibody produced by a hybridoma is unique to the knockout mouse, a first test is whether the same antigen provokes an antibody response in a wild-type mouse. A wild-type mouse, such as a C57BL/6, CD1, 129Sv, or most ideally, mice syngeneic to the knockout mice (obtained by employing sham or nontransfected ES cells in the same protocol as performed to generate null homozygotes), is immunized with the same antigen and on the same immunization schedule as the knockout mouse. Failure of the wild-type mouse to mount an antibody response to the antigen, assessed either by evaluation of the polyclonal (for example from blood) or monoclonal (for example from splenic cells fused to an appropriate partner cell) is prima facie evidence that the knockout mouse antibodies are unique to the knockout mouse. For example, if immunization of the knockout mouse results in antigen-specific IgG being produced and no antigen-specific IgG's are produced in the wild type mouse, then all antigen-specific IgG from the knockout are unique to that mouse strain.

If both the wild type and the knockout mouse render an antibody response to an antigen, then an antibody produced by the knockout mouse can be identified as unique to the knockout mouse using any number of techniques that allows detection of selective gene expression in specific cells or tissues. Such techniques include, but are not limited to, the following procedures:

A. KO unique mAb cDNA Library by Subtraction: Antibodies unique to the knockout mouse can be isolated and identified by the technique of subtractive cloning (L. Diatchenko et al. (1996) *Proc. Natl. Acad. Sci.* (*USA*) 93:6025-6030; Clontech PCR-Select™ cDNA Subtraction Kit User Manual [PT1117-1 (PR22926)] Published 14 Feb. 2002 Catalog #: K1804-1; D. V. Rebrikov et al. (2000) *Nucleic Acid Res.* 28: e90). In brief, mRNA is isolated from the B cell component of splenocytes separately from both the immunized wild type and knockout mice. Double stranded cDNA synthesis is then performed on each mRNA population using the template switch technique (SMART™ PCR cDNA Synthesis Kit; Clontech). After several other manipulations, the knockout and wild-type cDNA pools are pooled and subjected to PCR-driven suppression subtractive hybridization such that only sequences differentially expressed in the knockout mRNA population are obtained. These can be cloned and characterized by sequencing and hybridization. Antibody sequences remaining in the knockout library after suppressive subtraction are unique to the knockout mouse.

B. Screening DNA microarrays: A molecular profile of mRNAs present in the spleens of immunized mice can be obtained by means of DNA microarrays (R. Glynne et al. (2000) *Immunol Rev.* 176:216-246; C. G. Vinuesa et al. (2002) *Ann. N.Y. Acad. Sci.* 975:33-45; L. M. Staut (2003) *New Engl. J. Med.* 348:1777-1785). For this approach, mRNA is extracted from the B cell population of a wild-type mouse immunized with an antigen in a manner identical to the knockout mouse. Briefly, cDNA libraries are separately generated for each of the immunoglobulin CDR regions (heavy and light chain CDR-1, -2 and -3) by PCR with the appropriate framework primers. Each of these libraries is used to generate its own DNA microarray. For testing, each of the CDRs from the knockout antibody is used to generate a fluorescently labeled cDNA probe. This probe is then incubated on the surface of the DNA microarray for the corresponding wild-type CDR. The probe will hybridize to the corresponding CDR sequence in the wild type array, if present, which is detected with a scanning fluorescence microscope. If any of the knockout antibody CDR probes fail to give a signal with their corresponding CDR microarray, the antibody is unique to the knockout mouse.

C. Quantitative RT-PCR: Candidate antibodies from the knockout mouse are sequenced and that sequence is used, by comparison to known murine antibody sequences, to derive knockout antibody specific RT-PCR primers. These are used to prime RNA preparations from wild-type mouse spleens. Failure to detect a signal above background demonstrates that knockout antibody is unique to that mouse strain.

D. CDR Profiling: The candidate knockout antibody or antibodies are sequenced and the specific sequences of each of the six CDRs (3 heavy chain CDRs [H1, H2 and H3] and 3 light chain CDRs [L1, L2 and L3]) are obtained for each antibody. These sequences are compared to known or the determined ensemble of comparable murine CDRs from the wild type mouse. The latter is accomplished by utilizing the CDR fingerprint profiling technique (F. M. Raaphorst, J. Tami and I. E. Sanz (1996) *Biotechniques* 20:78-87; S. Desravines and E. Hsu (1994) *J. Immunol. Methods* 168:219-225). In brief, this technique calls for the enrichment of B cells, extraction and isolation of RNA, first strand cDNA synthesis and subsequent PCR amplification using 5' PCR primers located in the framework regions and 3' PCR primers located in the constant region. The PCR products can be size-separated and subsequently cloned and sequenced. A unique CDR not present in the wild type ensemble defines the knockout antibody as unique to the knockout mouse.

The hybridomas of the present invention may be used to produce monoclonal antibodies. This is achieved by the following steps: a) growing the hybridoma under conditions that promote the expression and secretion of said monoclonal antibody; and b) isolating said monoclonal antibody from the media in which the hybridoma is grown. The conditions for promoting expression and secretion of monoclonal antibodies from hybridomas are well known. These are typically growing the hybridomas in selective media (typically a HAT selection media) on feeder layers of macrophages that have been primed with incomplete Freund's adjuvant or the like several days before plating the hybridomas for about 7 to 14 days.

The hybridomas are then screened for the production of antibodies against the molecule of interest. This is typically achieved by using and ELISA or other colorimetric assay. Once a hybridoma producing a monoclonal antibody of interest is identified, it is typically recloned and reassayed. Hybridomas that are confirmed to be producing a KO unique mAb are then grown up in larger amounts in an appropriate medium, such as D-MEM or RPMI-1640. Alternatively, the hybridoma cells can be grown in vivo as ascites tumors in an animal.

After sufficient growth to produce the desired mAb, the growth media containing the KO unique mAb (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Amersham Biosciences, publication No. 18-1037-46, Edition AC, the disclosure of which is hereby incorporated by reference) The bound antibody is typically eluted from protein A/protein G columns by using low pH buffers (glycine or acetate buffers of pH 3.0 or less) with immediate neutralization of Ab-containing fractions. These fractions are pooled, dialyzed, and concentrated as needed.

According to an alternate embodiment, the DNA encoding the KO unique mAb is isolated from the hybridoma, placed in an appropriate expression vector for transfection into an appropriate host. The host is then used for the recombinant production of the KO unique mAb, or variants thereof, such as a humanized version of that monoclonal antibody, active fragments of the antibody or chimeric antibodies comprising the antigen recognition portion of the KO unique mAb. The KO unique mAb, and derivatives thereof produced by any of the above-described methods are another aspect of the present invention.

DNA encoding the monoclonal antibodies of the invention is readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant expression in bacteria of DNA encoding the antibody is well known in the art (see, for example, Skerra et al., Curr. Opinion in Immunol., 5, pp. 256 (1993); and Pluckthun, Immunol. Revs., 130, pp. 151 (1992).

The DNA also can be modified prior to insertion into an expression vector, for example, by substituting the coding sequence for human heavy- and light-chain constant domains in place of the homologous murine sequences (e.g., Morrison et al., Proc. Natl. Acad. Sci. U.S.A., 81, pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the KO unique mAb. Typically, such non-immunoglobulin polypeptides are substituted for the constant domains of an antibody of the invention.

Thus, according to another embodiment, the invention relates to a KO unique mAb that is humanized. "Humanized" forms of KO unique monoclonal antibodies according to this invention are specific chimeric immunoglobulins, immunoglobulin chains or fragments thereof (such as Fv, Fab, Fab', $F(ab')_2$, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the KO unique mAb (donor antibody) while maintaining the desired specificity, affinity, and capacity of the KO unique mAb. In some instances, Fv framework residues of the human immunoglobulin may be replaced by corresponding murine residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the KO unique mAb and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al., Nature, 332, pp. 323 (1988); and Presta, Curr. Op. Struct. Biol., 2, pp. 593 (1992).

Methods for humanizing the KO unique mAbs of this invention are well known in the art. Generally, a humanized antibody according to the present invention has one or more amino acid residues introduced into it from the KO unique mAb. These murine amino acid residues are often referred to as "import" residues, which are typically taken from an "import" variable domain. Humanization can be essentially performed following the method of Winter and co-workers (Jones et al., Nature, 321, pp. 522 (1986); Riechmann et al., Nature, 332, pp. 323 (1988); Verhoeyen et al., Science, 239, pp. 1534 (1988)). Accordingly, such "humanized" antibodies are chimeric antibodies (Cabilly et al., U.S. Pat. No. 4,816, 567), wherein substantially less than an intact human variable domain has been substituted by the corresponding sequence from the KO unique mAb. In practice, humanized antibodies according to this invention are typically human antibodies in which some CDR residues and possibly some FR residues are substituted by residues from analogous sites in the KO unique mAb.

The choice of human variable domains, both light and heavy, to be used in making the humanized antibodies is preferred to reduce antigenicity. According to the so-called "best-fit" method, the sequence of the variable domain of a KO unique mAb is screened against the entire library of known human variable-domain sequences. The human sequence which is closest to that of the mouse is then accepted as the human framework (FR) for the humanized antibody (Sims et al., J. Immunol., 151, pp. 2296 (1993); Chothia and Lesk, J. Mol. Biol., 196, pp. 901 (1987)). Another method uses a particular framework from the consensus sequence of all human antibodies of a particular subgroup of light or heavy chains. The same framework can be used for several different humanized antibodies (Carter et al., Proc. Natl. Acad. Sci. U.S.A., 89, pp. 4285 (1992); Presta et al., J. Immunol., 51, pp. 1993)).

It is further preferred that antibodies be humanized with retention of high affinity for the molecule of interest and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Another method of making "humanized" monoclonal antibodies is to use a XenoMouse® (Abgenix, Fremont, Calif.) as the knockout mouse. A XenoMouse is a murine host according to this invention that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

The KO unique monoclonal antibodies of the present invention may also be derivatized to "chimeric" antibodies (immunoglobulins) in which a portion of the heavy and/or light chain is identical with or homologous to corresponding sequences in the KO unique mAb, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., *Proc. Natl. Acad. Sci. U.S.A.*, 81, pp. 6851 (1984)).

According to yet another embodiment, the invention provides immunoreactive fragments of the KO unique mAbs. "Immunoreactive fragments" comprise a portion of the intact KO unique monoclonal antibody, generally the antigen binding site or variable region. Examples of antibody fragments include Fab, Fab', Fab'-SH, F(ab)$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments.

According to another embodiment, the intact KO unique mAbs, humanized forms of KO unique mAbs, immunoreactive fragments of KO unique mAbs or chimeric antibodies comprising an immunoreactive portion of the KO unique mAb (hereinafter referred to as "monoclonal antibodies according to this invention") are formulated into a composition. The composition comprises an amount of a monoclonal antibody of this invention effective to detectably reduce or eliminate the activity of the molecule of interest in a patient or in a biological sample. The composition further comprises a pharmaceutically acceptable carrier.

The term "biological sample" as used herein includes cell cultures or extracts thereof; biopsied material obtained from a mammal or extracts thereof; and blood, saliva, urine, feces, semen, tears, or other body fluids or extracts thereof.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of this invention may be employed in a method of inhibiting the activity or function of a molecule of interest in a patient or a biological sample. This method comprises the step of contacting said composition with said patient or biological sample. Such method will be useful for both diagnostic and therapeutic purposes.

For use in conjunction with a biological sample, the composition can be administered by simply mixing with or applying directly to the sample, depending upon the nature of the sample (fluid or solid). For use in conjunction with a patient, the composition must be formulated for administration to the patient.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the compositions may be formulated in an ointment such as petrolatum.

The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

According to yet another embodiment, the monoclonal antibodies of this invention may be conjugated or covalently bound to a toxin, such as ricin, diphtheria toxin, abrin and *Pseudomonas* exotoxin to a detectable moiety, such as a fluorescent moiety, a radioisotope or an imaging agent or to a solid support, such as agarose beads or the like. Methods for conjugation or covalent bonding of these other agents to the monoclonal antibodies are well known in the art.

Conjugation to a toxin is useful for targeted killing of cells displaying the molecule of interest on their cell surface. Once the monoclonal antibody of the invention binds to the cell surface of such cells, it is internalized and the toxin is released inside of the cell, selectively killing that cell.

Conjugation to a detectable moiety is useful when the monoclonal antibody of this invention is used for diagnostic purposes. Such purposes include, but are not limited to, assaying biological samples for the presence of the molecule of interest and detecting the presence of the molecule of interest in a living organism.

Conjugation of a monoclonal antibody of this invention to a solid support is useful as a tool for affinity purification of the molecule of interest from a source, such as a biological fluid, a cell culture supernatant or a solubilized tissue.

In an alternate embodiment, the monoclonal antibodies of this invention may be incorporated into liposomes ("immunoliposomes"), together with another substance for targeted delivery to an animal. Such other substances include nucleic acids for the delivery of genes for gene therapy or for the delivery of antisense RNA, RNAi or siRNA for suppressing a gene in a specifically targeted cell, or toxins or drugs for the targeted killing of cancer cells or infectious agents.

In order that the invention described herein may be more fully understood, the following examples are set forth. It should be understood that these examples are for illustrative purposes only and are not to be construed as limiting this invention in any manner.

Example 1

Generation of Novel mAbs Against P-Selectin Glycoprotein Ligand-1 (PSGL-1)

PSGL-1 is an important counter-receptor for P-, E- and L-selectin. Its physiological role is to mediate the extravasation of leukocytes (white blood cells) to sites of inflammation. Blockage of PSGL-1: selectin interactions inhibits leukocyte extravasation. Thus, monoclonal antibodies which block such interactions could be of potential therapeutic use (e.g. A. E. Hicks et al. (2003) *Blood* 101:3249-3256; J. W. Phillips et al. (2003) *Circulation* 107:2244-2249).

Human PSGL-1 is purified from HL-60 cells by well-known methods (see, for example, P. P. Wilkins et al. (1996) *J. Biol. Chem.* 271: 18732-18742). In brief, PSGL-1 is extracted from cells and passed over a column of immobilized P-selectin. The affinity column is washed and the bound PSGL-1 is eluted with EDTA. Fractions containing PSGL-1 are dialyzed against a calcium-containing buffer and passed a second time over the same column. The column is again washed and eluted with an EDTA buffer. The purity of the PSGL-1 preparation is checked by SDS-polyacrylamide gel electrophoresis (SDS-PAGE) under both reducing and non-reducing conditions.

The glycosyltransferase "Core 2" [core 2 $\beta$1-6-N-glucosaminyltransferase (C2GlcNAcT-I; EC 2.4.1.102)] is a critical enzyme for the biosynthesis of functional PSGL-1 (M. P. Bernimoulin et al. (2003) *J. Biol. Chem.* 278:37-47; R. Kumar et al. (1996) *Blood* 88: 3872-3879), catalyzing the branching of O-linked oligosaccharides on glycoprotein substrates. There are three known core 2 enzymes, denoted Core 2L, core 2M and core 2C, but branched oligosaccharides in leukocytes are formed only by the core 2L enzyme. A knockout mouse with a targeted deletion of the core 2L gene has been shown to exhibit impaired leukocyte extravasation in vivo (L. G. Ellies et al. (1998) *Immunity* 9:881-890; M. Sperandio et al. (2001) *Blood* 97:3812-3819).

Immunization of knockout and wild-type mice: Separate pools of four core 2L knockout or wild type (generated in a manner identical to the knockout mice except that the ES cells are transfected with a sham vector) mice are initially immunized with 25 μg of purified PSGL-1 per mouse by subcutaneous (s.c.) injection of 0.2-0.3 ml of a mixture of equal parts Freund's complete adjuvant and protein solution. After at least two weeks, and as much as several weeks being acceptable, mice in each pool are again immunized as above except for using Freund's incomplete adjuvant. After a further 2-3 weeks, the mice are again immunized as in the second immunization, except that the antigen mixture is administered intravenously (i.v.). At 4 days after the final immunization, all mouse tails are bled. The blood is then diluted to 1:40 with PBS, and an ELISA is performed to detect antibodies against PSGL-1. The mice with the strongest immune response in each group are selected for removal of spleens and the creation of monoclonal antibodies.

Removal of spleens and collection of B cells: Each removed spleen is placed in a dish containing a screen with 10 ml of Dulbecco's modified Eagle medium (DMEM). Using the plunger of a 5 ml syringe, the spleen cells are quickly and carefully dispersed against the screen. While leaving the connective tissue on the grid, the dispersed cells are pipetted up and down and then places into a 15 ml conical tube. Any large chunks are allowed to settle to the bottom of the tube for 2-3 min. Cells isolated from the same type of mouse (knock out or wild type), can be added to the same conical tube. The supernatants are transferred to another tube and the volume adjusted up to 15 ml with DMEM. The cell suspensions are then washed by centrifugation for 10 min at 170×g on a table-top centrifuge. Supernatants are then carefully removed with a sterile Pasteur pipette. Spleen cells are then washed again with 10 ml DMEM. The resulting cell pellet is resuspended in 5 ml of DMEM and then incubated for 10 minutes at 37° C. For each pool of spleen cells (knockout or wild type) 1 ml of spleen cells is inoculated into 10 tissue culture flasks containing DMEM. The flasks are then incubated overnight in 6% $CO_2$ in a 37° C. chamber.

Preparation for Fusing Spleen Cells with SP2/0 Cells: SP2/0 cells (in 10 tissue culture plates) are triturated, harvested and put into 2×50 ml conical tubes. The tubes are centrifuged to pellet the cells (×170 g; 10 min.) and the cells are then washed three times. The SP2/0 cells are resuspended in a final volume of 10 ml and counted. In the meantime, the spleen cells are pelleted and washed three times. Finally, the spleen cell pellet is incubated for 10 minutes at 37° C., resuspended in 20-30 ml, and counted.

Fusing spleen and SP2/0 cells: A volume equivalent to $1 \times 10^8$ spleen cells is then added to a volume of resuspended SP2/0 cells equivalent to $5 \times 10^7$ SP2/0 cells. The mixture of SP2/0 and spleen cells is centrifuged at 200×g. The supernatant is discarded and 1.5 ml of polyethylene glycol is added over a period of 1 minute with agitation. The mixture is stirred gently with tip of pipette to mix in the PEG for another 90 seconds. One ml of warmed DMEM is then added over 1 minute while stirring. The previous steps are repeated by centrifuging the cells at 200×g for 10 minutes and re-adding PEG, and then adding 8 ml DMEM over 5 minutes. After 10 minute, the cells are disrupted by pipetting gently 5 times. The disrupted cells are diluted into sterile filtered DMEM containing the feeder layer cells and aliquoted 2 ml/well into 24 well plates (~10-12 plates). The plates are incubated in a 6% $CO_2$ incubator at 37° C., replacing the feeder layer once a week.

Screen Fusions by ELISA: Three weeks after the cell fusion, the supernatants from each tissue culture well are tested for the presence of antibodies against the purified PSGL in an ELISA (enzyme linked immunosorbent assay) test using a standard protocol. Wells that are positive by ELISA are then grown up in larger plates and then re-tested by ELISA. Positive plates are split with half of the cells being frozen in 10% DMSO as backups and the other half being diluted into a 96 well plate at a dilution of 1 cell to ±3 wells. After the cells begin to grow in the 96 well plates they are transferred to 24 well plates and retested by ELISA. Positive wells are again diluted into 96 well plates until all wells containing cells test positive by ELISA. Cells are then weaned from 10% FCS to 5% FCS, and from HAT to HT to unsupplemented media.

Assay for mAbs blocking P-selectin/PSGL-1 adhesion: KO-specific monoclonal antibodies that block selectin binding to PSGL-1 are identified using a cell-based adhesion assay performed under conditions of low shear flow as described by Snapp et al. (K. R. Snapp et al., (1998) *Blood* 91:154-164). Chinese hamster ovary ("CHO") cells expressing P-selectin or E-selectin monolayers were grown to confluence on glass coverslips and inserted into a flow chamber. A defined flow level of 1.8 dynes/cm2 was obtained by drawing media containing the desired cell population through the chamber using a syringe pump. Purified human neutrophils ($1 \times 10^6$) were assayed in each experiment. The flow chamber was mounted on an inverted microscope (Nikon Diaphot; Melville, N.Y.) and each 5-minute perfusion period was recorded on videotape by a video camera and video cassette recorder. Leukocyte adhesion was determined as previously described (F. W. Lucinskis et al., (1996) *J. Immunol.* 157:326-335).

Identification of mAbs as Knock-out-Specific: Hybridomas derived from the spleens of knock out or wild type mice are independently cultured to generate sufficient cells to allow individual extraction of their mRNAs, conversion to cDNAs, cloning and nucleotide sequencing of the antibody transcripts. Antibody sequences found only in the KO pool but not in the wild type pool are defined as KO specific.

Example 2

Generation of Novel Anti-Cancer mAbs in GnT-V Knock Out Mice

As noted by Hakamori ([2002] *Proc. Natl. Acad. Sci. (USA)* 99:10231-10233), "Aberrant glycosylation occurs in essentially all types of experimental and human cancers, as has been observed for over 35 years, and many glycosyl epitopes constitute tumor-associated antigens." For example, the epithelial cell surface protein MUC 1 (CD227) is a heavily glycosylated mucin composed of tandem mucin domain repeats, each containing five potential sites of O-glycosylation. The expression of MUC1 is elevated in a number of cancers, including those of breast, lung, colon, and pancreas (S. J. Gendler *J. Mammary Gland Biol. And Neoplasia* 6:339-353 (2001). In cancer, the O-glycosylation of MUC1 is altered; changing from highly elaborated and branched structures to shorter, unbranched, sialylated structures (F.-G Hanisch et al. *Eur. J. Biochem.* 236, pp. 318-327 (1996). In addition, the number of potential sites of O-glycosylation employed on MUC1 is reduced in cancer, exposing previously cryptic peptide epitopes that cause the presence of MUC1 peptide-specific IgG and IgM in the sera of some patients (Y. Kotera et al., *Cancer Res.* 54:2856-2860 (1994). The presence of such antibodies is a positive prognostic indicator (Y. Hamanaka et al., *Int. J. Cancer* 103, pp. 97-100 (2003)).

In another example, the glycosyl epitopes sialyl Lewis X ($SLe^X$) and sialyl Lewis A ($SLe^A$) are known tumor-associated antigens whose expression is inversely correlated with postoperative survival rate of patients (S. Nakamori et al., *Cancer Res.* 53, pp. 3632-3637 (1993); R. Kannagi *Glycoconj. J.* 14, pp. 577-584 (1997)).

Moreover, cancer-associated altered glycosylation can have important functional roles for disease progression, particularly for the processes of invasion and metastasis where cancer cells migrate from a primary tumor to other tissues.

For example, elaboration of N-linked oligosaccharides is an important component for the growth of cancer cells and their metastasis to secondary organs (see Hakamori, 2002). The enzyme β1,6-N-acetylglucosaminyltransferase V (GnT-V) catalyzes the formation of one specific branch on asparagine-linked oligosaccharides attached to cell surface and secreted proteins. The various products resulting from the action of other glycosyltransferases downstream of GnT-V are enhanced in malignancies and correlate with disease progression (W. K. Seelentag et al. *Cancer Res.* 58:5559-5564 (1998)). In an "oncomouse" model of breast cancer, targeted deletion of GnT-V retards tumors growth and oblates metastasis to secondary sites (Granovsky et al. *Nature Medicine* 6:306-312 (2000)).

Unfortunately, most of the cancer-associated glycosylation changes are not very immunogenic. Thus, efforts to raise antibodies or generate vaccines using cancer-associated glycosyl epitopes are difficult and limited in their scope. For example, MUC1-derived glycopeptides effectively generate a T cell response only when the peptide component is re-engineered to enhance interactions with MHC class II molecules (M. Gad et al. *Eur. J. Immunol.* 33:1624-1632 (2003)) or when the cancer-associated carbohydrates are linked to keyhole limpet hemocyanin (KLH), haptenizing the antigen, and the conjugate used as a vaccine (D. Miles et al., *Clin. Breast Cancer* 3:S134-S138 (2003)). Thus, the use of appropriate mice, genetically engineered to have an altered definition of "self" in terms of tumor-associated glycan structures, will allow the isolation of potent monoclonal antibodies for use as cancer therapeutics.

Immunization of knockout and wild-type mice: Separate pools of four GnT-V knockout or wild type (generated in a manner identical to the knockout mice except that the ES cells are transfected with a sham vector) mice are initially immunized with 25 µg (protein) of the total membrane preparation from human breast cancer tumors. Each mouse is given a subcutaneous (s.c.) injection of 0.2-0.3 ml of a mixture of equal parts Freund's complete adjuvant and the total membrane preparation. After at least two weeks, and as much as several weeks being acceptable, mice in each pool are again immunized as above except for using Freund's incomplete adjuvant. After a further 2-3 weeks, the mice are again immunized as in the second immunization, except that the antigen mixture is administered intravenously (i.v.). At 4 days after the final immunization, all mouse tails are bled. The blood is then diluted to 1:40 with PBS and an ELISA is performed to detect antibodies against the tumor membrane preparation. The mice with the strongest immune response in each group are selected for removal of spleens and the creation of monoclonal antibodies.

Removal of spleens, isolation of RNA: Splenocytes are prepared for each pool of animals (KO or wild type) essentially as described by B. Hunt et al. in "Monoclonal antibodies: Preparation and Use of Monoclonal Antibodies and Engineered Antibody Derivatives" [H. Zola, Ed.] 2000, Springer-Verlag, New York). The mouse is euthanized by $CO_2$ inhalation and the spleen removed aseptically after soaking the cadaver in 70% ethanol. The spleen is transferred to a Petri dish containing DMEM containing 2% fetal bovine serum (FBS). Any remaining fat or connective tissue is trimmed away. After making incisions through the spleen capsule, splenocytes are dispersed by gently agitating with the tip of a sterile pipette. The suspension is transferred to a loose fitting homogenizer containing 10 ml of DMEM+2% FBS and gently homogenized by hand until a uniform cell suspension is formed. The suspension is transferred to a 50 ml centrifuge tube. The homogenizer is rinsed with 10 ml of DMEM+2% FBS and this is added to the centrifuge tube. The capsule is removed from the pooled suspension. The suspension is centrifuged for 3 minutes at 90×g and the supernatant decanted. The pellet is rewashed with 10 ml of serum-free DMEM, centrifuged, and the pelleted cells are resuspended once more in 10 ml of serum-free DMEM.

Total RNA is prepared using an RNA isolation kit from Promega (Madison, Wis.), and cDNA synthesis is performed with Superscript II (Life Technologies Inc., Paisley, UK) according to the method of J. Engberg et al., *Mol. Biotechnol.* 6, pp. 287-310 (1996)) using 50 µg RNA per reaction.

Generation of a KO-specific scFv immunoglobulin library by subtractive hybridization: Immunoglobulin CDRs contained within the KO-specific library are inserted within a master immunoglobulin framework of a human IgG1. This is performed essentially as described by E. Soderlind et al., *Nat. Biotechnol.* 8:852-856 (2000) for placing CDR libraries into a scFv framework. The cDNA synthesis reaction is primed with 3' primers specific for the murine γ, µ, α, κ and λ constant regions (described at www.mrc-cpe.cam.ac.uk/mouse_gene.php). For each CDR a pair of primers homologous to the master framework is used. Each of the six CDRs is PCR amplified using TaqPlus Precision PCR System (Stratagene, La Jolla, Calif.), according to the manufacturer's instructions. Thus, 12 CDR libraries are made, six from the KO mice and six from the wild-type mouse. The six libraries for each mouse type are composed of a specific library for each heavy chain CDRs (CDR-H1, —H2, and H3) and each light chain CDR (CDR-L1, L2 and L3). A KO-specific library for each of the six CDRs is then generated using the technique of suppression subtractive hybridization (SHH) with mirror orientation selection (MOS) (D. V. Rebrikov et al., *Nucleic Acids Res.* 28:E90 (2000)) using the KO mouse CDR library as the target and the wild type CDR library as the driver. The resulting six KO-specific CDR libraries are pooled and combinatorially assembled into scFv genes with a common human immunoglobulin framework template as described by E. Soderlind et al., supra.

The assembled scFv antibody gene fragments are purified using QIAquick PCR Purification Kit (Qiagen), digested with SfiI and NotI (New England Biolabs, Beverly, Mass.), and purified using QIAquick Gel Extraction Kit (Qiagen). They are then ligated into the NotI/SfiI sites in a pFAB5c-His vector and transformed into electrocompetent TOP10F' *E. coli* cells. Amplification of the library and phage stock production with R408 helper-phage is done as described by J. Engberg et al., *Mol. Biotechnol.* 6:287-310 (1996)). Phage which bind with high affinity to the membrane extract of cancer cells are identified from the phage libraries by subtractive selection (B. Stausbol-Gron et al., *Eur. J. Biochem.* 268:3099-3107 (2001)). These scFvs can be incorporated into liposomes ("immunoliposomes") for the targeted delivery of genes for gene therapy or drugs for cancer chemotherapy (J. W. Parks et al., *J. Control. Release.* 74:95-113 (2001); L. Xu et al., *Mol. Cancer. Ther.* 1:337-346 (2002); C. Sun et al., *Bioorg Med. Chem.* 11:1761-1768 (2003)).

Example 3

Generation of Novel Anti-Infectives in Galactosyltransferase(β1,4)-I Knock Out Mice The ability of infectious agents to be successful is dependent upon factors specific to the pathogen, the human host, and the complex interactions between host and pathogen. An important example of the latter is the game of "hide and seek" played out between infectious agents and the immune system (e.g. M. T. Vossen et al., *Immunogenetics*, 54:527-42 (2002); J. Pieters, *Curr Opin Immunol.* 13:37-44 (2001)).

One mechanism of host immune evasion is molecular mimicry where a pathogen creates and presents on its surface molecules that are like those of the host. Thus camouflaged, the host immune system fails to respond to the pathogen because the latter appears to be "self" (C. E. Stebbins and J. E. Galan, *Nature* 412:701-705 (2001); P. M. Murphy *Nat. Immunol.* 2:116-122 (2001)).

Many examples of molecular mimicry are known both for bacterial and viral pathogens. *Campylobacter jejuni* is a mucosal pathogen that has been recognized as an important cause of acute gastroenteritis in humans (B. M. Allos *Clin. Infect. Dis.* 32:1201-1206 (2001)) and has been shown to have variable cell-surface carbohydrates that are associated with virulence (D. J. Bacon et al., *Mol. Microbiol.* 40:769-777 (2001)). *C. jejuni* is thought to be the most frequent infection preceding the development of Guillain-Barr syndrome (GBS). The core oligosaccharides of low molecular weight lipo-oligosaccharides (LOS) of many *C. jejuni* strains have been shown to exhibit molecular mimicry of the carbohydrate moieties of gangliosides (M. Gilbert et al., *J. Biol. Chem.* 277:327-337 (2002)). The molecular mimicry between *C. jejuni* LOS outer core structures and gangliosides has also been suggested to act as a trigger for autoimmune mechanisms in the development of Guillain-Barr syndrome (N. Yuki et al., *Biomed. Res.* 13: 451-453 (1992)).

The LOS of pathogenic *Neisseria* (e.g., *N. meningitidis* and *N. gonorehae*) and *Haemophilus* (e.g. *H. somnus* and *H. influenzae*) species express carbohydrate moieties that mimic the carbohydrates of glycosphingolipids on human cells (A. P. Moran et al., *FEMS Immunol. Med. Microbiol.* 16:105-115 (1996); M. P. Jennings et al., *Mol. Microbiol.* 18:729-740 (1995)). Specifically, these pathogen structures are immunologically or structurally identical to the human lacto-N-neotetraose determinant. These pathogen structures can be subsequently modified by sialylation further enhancing their mimicry of human glycan structures. Sialylation of pathogen mimics of lacto-N-neotetraose has been shown to increase pathogen resistance to complement and reduce the binding of anti-LOS antibodies (J. P. van Putten, *EMBO J.* 12:4043-4051 (1993); T. J. Inzana et al., *Infect. Immun.* 70:4870-4879 (2002); W. M. Shafer et al., *J. Endotoxin Res.* 8:47-58 (2002))

Pathogenic viruses also can employ the glycosylation apparatus of the infected host to mask themselves from immune responses. A well-known example of this is HIV which has been proposed to employ an evolving "glycan shield" to escape host antibody responses, specifically antibodies that will neutralize the virus (X. Wei et al., *Nature* 422:307-312 (2003)). As the host develops new neutralizing antibodies to the virus, new asparagine-linked glycosylation sites emerge, especially on the viral glycoprotein gp130 that binds to the virus receptor CD4, to mask the neutralization epitope. Because the host produces the N-linked glycans on HIV gp120, they are recognized as "self" and are not immunogenic. Sometimes, however, an unusual "clustering" of these asparagines-linked glycans can form an immunogenic epitope, though recognized by antibodies with an unusual architecture (D. A. Calarese et al., *Science* 300: 2065-2071 (2003)).

The altered antibody repertoire of mice with a genetically engineered defect in the enzyme β(1,4)-galactosyltransferase I (β4GalT-I; UDP-Gal:N-acetylglucosamine (β1,4-galactosyltransferase I) is used to identify novel KO-specific antibodies to pathogens, such as HIV.

β4GalT-I is one member of the β4GalT family of enzymes that catalyze the addition of galactose residues in a β1,4 linkage to acceptor oligosaccharides. To date, seven β4GalT genes (β4GalT-I to -VII) have been identified (T. Hennet, *Cell Mol. Life. Sci.* 59:1081-1095 (2002)) though the individual biosynthetic roles for some members have yet to be defined. β4GalT-VII acts on xylose (to form proteoglycans). Thus, β4GalT-I to -VI must catalyze the formation of the Gal β1,4-Glc-NAc-R linkage in N- and O-linked oligosaccharides. These latter structures include selectin ligands such as $SLe^X$ and 6-sulfo-$SLe^X$ (M. Asano et al., *Blood* 102:1678-1685 (2003)). It has been demonstrated that β4GalT-I KO mice are deficient in the normal elaboration of complex-type N-linked oligosaccharides and certain O-linked oligosaccharides including O-linked $SLe^X$ (N. Kotani et al., *Biochem J.* 357: 827-834 (2001); N. Kotani et al., *Biochem. Biophys. Res. Commun.* 260:94-98 (1999)). In contrast, other Gal(β1,4) glycoconjugates, such as those found in PSA and HNK-1, are expressed normally and no neuronal defects are detected in β4GalT-I-deficient mice (M. Kido et al., *Biochem. Biophys. Res. Commun.* 245:860-864 (1998)). This suggests that a β4GalT gene(s) other than β4GalT-I is responsible for the biosynthesis of these molecules. Thus, β4GalT-I KO mice are missing many, though not all, of the terminal elaborations of N- and O-linked protein-linked oligosaccharides that serve as ligands for numerous cell-cell or protein-cell interactions. β4GalT-I KO mice possess an enhanced immune repertoire that reflects at least the sum of individual contributions from each of these absent determinants.

Generation of β-GalT-I KO mice: Mice with a targeted deletion of the βGalT-I gene are prepared according to the literature (M. Asano et al. *EMBO J.* 16:1850-1857 (1997); Q. Lu and B. D. Shur, *Dev. Biol.* 181:257-267 (1997)). Mice with this targeted deletion show growth retardation and semi-lethality before weaning because of the augmented proliferation and abnormal differentiation of small intestinal epithelial cells (M. Asano et al., supra). However, a sufficient number of homozygotes survive to allow a colony to be founded and maintained. Mice are housed and maintained in a pathogen-free environment.

Isolation of recombinant gp120 from CHO cells: The viral envelope gp120 from HIV-$1_{CM235}$ is produced recombinantly in CHO cells as previously described (N. L. Haigwood et al., *J. Virol.* 66:172-182 (1992); T. C. VanCott et al. *J. Virology* 73:4640-4650, (1999)). HIV-$1_{CM235}$ is a primary isolate that uses the chemokine receptor CCR5 as a co-receptor and was originally isolated by co-cultivation in peripheral blood mononuclear cells (PBMC) from a subtype E HIV-1-infected individual living in Chiang Mai, Thailand (F. E. McCutchan et al., *AIDS Res. Hum. Retroviruses* 8:1887-1895 (1992)). Recombinant $gp120_{CM235}$ induced antibodies preferentially reactive with native gp120, bound to multiple subtype B and E gp120 strains, and neutralized both subtype B and subtype E-T-cell line-adapted (TCLA) isolates (T. C. VanCott et al., supra). Recombinant $gp120_{CM235}$ thus produced is correctly glycosylated, binds CD4, and is greater than 90% pure.

Immunization of knockout and wild-type mice: Separate pools of four β4GalT-I knockout or wild type (generated in a manner identical to the knockout mice except that the ES cells are transfected with a sham vector) mice are initially immunized with 25 μg (protein) of $gp120_{CM235}$ per mouse by subcutaneous (s.c.) injection of 0.2-0.3 ml of a mixture of equal parts Freund's complete adjuvant and the total membrane preparation. After at least two weeks, and as much as several weeks being acceptable, mice in each pool are again immunized as above except for using Freund's incomplete adjuvant. After a further 2-3 weeks, the mice are again immunized as in the second immunization, except that the antigen mixture is administered intravenously (i.v.). At 4 days after the final immunization, the tails from all the mice are bled. The blood is then diluted to 1:40 with PBS, and an ELISA is performed to detect antibodies against gp120$_{CM235}$. The mice with the strongest immune response in each group are selected for removal of spleens and the creation of monoclonal antibodies.

Removal of spleens and collection of B cells: Spleens from wild-type mice are removed and set aside for the isolation of mRNA and creation of a "wild-type" spleen cDNA library for use in CDR-profiling (see below). Spleens from KO mice exhibiting a strong immune response are used to collect B cells as described in Example 1. The methods for generating monoclonal antibodies through the preparation of spleen cells for fusion with SP2/0 cells, the actual fusing of spleen and SP2/0 cells and the screening of hybridomas by ELISA are also performed essentially as described in Example 1.

Identification of mAbs as Knock-out-Specific by CDR profiling: Candidate knockout-specific antibodies are sequenced and the specific sequences of each of the six CDRs (3 heavy chain CDRs [H1, H2 and H3] and 3 light chain CDRs [L1, L2 and L3]) are obtained for each antibody. These sequences are compared to known or the determined ensemble of comparable murine CDRs from the wild type mouse. The latter is accomplished with the CDR fingerprint profiling technique (F. M. Raaphorst et al., *Biotechniques* 20:78-87 (1996); S. Desravines and E. Hsu, *J. Immunol. Methods* 168:219-225 (1994)). This technique comprises enrichment of B cells from the spleens of immunized wild-type mice, extraction and isolation of RNA, first strand cDNA synthesis and subsequent PCR amplification using 5' PCR primers located in the appropriate framework regions and 3' PCR primers located in the constant region, as described in Example 2. The PCR products are size-separated and size-selected by comparison to the specific KO mAb CDR by gel electrophoresis. Selected PCR products from the wild-type mAb CDRs are subsequently cloned and sequenced. A KO-derived CDR not present in the wild type ensemble defines the knockout antibody as unique to the knockout mouse.

HIV-1 neutralization assay: To assess the function of isolated KO-specific mAbs, a HIV neutralization assay is performed. Neutralization assays, using H9 target cells for TCLA viruses or stimulated PBMC targets for primary isolates, are performed as described elsewhere (J. R. Mascola et al., *AIDS Res. Hum. Retroviruses* 12:1319-1328 (1996); J. R. Mascola et al., *J. Infect. Dis.* 173:340-348 (1996)). Briefly, test sera and virus inoculum are preincubated for 30 minutes prior to addition of target cells. After overnight incubation, cells are washed and resuspended in appropriate culture media. Virus growth is monitored by ELISA measurement of p24 antigen in culture supernatants, and neutralization is determined during the early virus growth phase (days 4 to 6). Pre- and post-immune mouse sera/hybridoma supernatants are directly compared in all assays at a dilution of 1:10 in the presence of virus and a final dilution of 1:20 after the addition to target cells. Data represented as fold reduction are derived by the ratio of p24 antigen in pre-immune sera to that in post-immune sera. Thus, a 10-fold reduction in p24 antigen indicates 90% neutralization. All sera are complement-depleted by heat inactivation at 56° C. for 40 min prior to use. Subtype B TCLA viruses MN, IIIB, SF2, and RF are obtained from the NIH AIDS Research and Reference Reagent Program.

While a number of embodiments of this invention are described herein, it is apparent that the basic examples may be altered to provide other embodiments of this invention. Therefore, it will be appreciated that the scope of this invention is to be defined by the appended claims rather than by the specific embodiments that have been represented by way of example.

What is claimed is:

1. A method of producing a monoclonal antibody that specifically binds to an epitope on a molecule of interest, wherein the epitope is not present naturally in a wild-type murine host, comprising the steps of:
   immunizing a knockout murine host with an antigen that comprises the epitope present on said molecule of interest in a manner sufficient for said knockout murine host to develop antibodies against said antigen, wherein said knockout murine host comprises a knockout mutation in an enzyme involved in a post-translational modification of a polypeptide or a modification of a lipid; and wherein in the wild-type murine host the modified portion of the polypeptide or lipid is exposed on a cell surface or exposed on a secreted molecule;
   isolating the splenocytes from said immunized knockout murine host and fusing said splenocytes with immortalized cells to form a hybridoma; and
   assaying said hybridoma to determine if it produces the monoclonal antibody,
   wherein when the wild-type murine host is immunized with the antigen it does not produce a monoclonal antibody that binds to the epitope, and
   wherein said knockout murine host is selected from a mouse having a knockout mutation in mannosyl (α1,6-)-glycoprotein β1,6-N-acetyl-glucosaminyltransferase V (MGAT5; GNT-V), a mouse having a knockout mutation in core 2 β1-6N-acetylglucosaminyltransferase (C2 GlcNAcT), and a mouse having a knockout mutation in β(1,4)-galactosyltransferase 1 (β4GalT-I).

2. The method according to claim 1, wherein said antigen is a viral envelope antigen.

3. The method according to claim 2, wherein said antigen is HIV viral envelope gp120.

4. In a method of producing a monoclonal antibody that specifically binds to an epitope on a molecule of interest, wherein the epitope is not present in a wild-type murine host, the method comprising the steps of: immunizing a murine host with an antigen that comprises the epitope present on said molecule of interest; allowing the murine host to develop antibodies to said antigen; isolating the splenocytes of said murine host;
   fusing said splenocytes with immortalized cells to form a hybridoma; and
   assaying individual hybridoma cells to determine if said hybridoma cell produces the monoclonal antibody, the improvement comprising utilizing a knockout murine host comprising a knockout mutation in an enzyme involved in a post-translational modification of a polypeptide or a modification of a lipid, wherein in the wild-type murine host the modified portion of the polypeptide or lipid is exposed on a cell surface or is exposed on a secreted molecule; and
   wherein when the wild-type murine host is immunized with the antigen it does not produce a monoclonal antibody that binds to the epitope, and
   wherein said knockout mutation is in an enzyme selected from mannosyl (α1,6-)-glycoprotein β1,6-N-acetyl-glucosaminyltransferase V (MGAT5; GNT-V), core 2 β1-6N-acetylglucosaminyltransferase (C2 GlcNAcT), and β(1,4)-galactosyltransferase I (β4GalT-I).

5. The method according to claim 4, wherein said antigen is a viral envelope antigen.

6. The method according to claim 5, wherein said antigen is HIV viral envelope gp120.

7. A method of producing a monoclonal antibody comprising the steps of:

growing a hybridoma under conditions that promote the expression by the hybridoma of a monoclonal antibody, wherein the hybridoma comprises a B cell from a knockout murine host that has been immunized with an antigen that comprises an epitope present on a molecule of interest, wherein:

the epitope is not present naturally in a wild-type murine host;

the knockout murine host comprises a knockout mutation in an enzyme involved in a post-translational modification of a polypeptide or a modification of a lipid, wherein in the wild-type murine host the modified portion of the polypeptide or lipid is exposed on a cell surface or exposed on a secreted molecule; and wherein the antibody specifically binds to an epitope that is not present naturally in the wild-type mouse; and when the wild-type murine host is immunized with the antigen it does not produce a monoclonal antibody that binds to the epitope; and isolating said monoclonal antibody from media in which said hybridoma is grown, and wherein said knockout murine host is selected from a mouse having a knockout mutation in mannosyl ($\alpha$1,6-)-glycoprotein $\beta$1,6-N-acetyl-glucosaminyltransferase V (MGAT5; GNT-V), a mouse having a knockout mutation in core 2 $\beta$1-6N-acetylglucosaminyltransferase (C2 GlcNAcT), and a mouse having a knockout mutation in $\beta$(1,4)-galactosyltransferase 1 ($\beta$4GalT-I).

* * * * *